(12) United States Patent
Miyazaki et al.

(10) Patent No.: US 7,968,874 B2
(45) Date of Patent: Jun. 28, 2011

(54) ORGANIC ELECTROLUMINESCENT DEVICE MATERIAL AND ORGANIC ELECTROLUMINESCENT DEVICE

(75) Inventors: Hiroshi Miyazaki, Fukuoka (JP); Atsuhiko Katayama, Fukuoka (JP); Shinji Matsuo, Fukuoka (JP); Katsuhide Noguchi, Fukuoka (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 221 days.

(21) Appl. No.: 12/438,304

(22) PCT Filed: Aug. 28, 2007

(86) PCT No.: PCT/JP2007/066639
§ 371 (c)(1),
(2), (4) Date: Feb. 20, 2009

(87) PCT Pub. No.: WO2008/029670
PCT Pub. Date: Mar. 13, 2008

(65) Prior Publication Data
US 2010/0181553 A1    Jul. 22, 2010

(30) Foreign Application Priority Data

Aug. 31, 2006 (JP) ................................. 2006-235274

(51) Int. Cl.
*H01L 21/00* (2006.01)
(52) U.S. Cl. ................ 257/40; 257/98; 257/E51.022; 438/82; 438/99
(58) Field of Classification Search .............. 257/40, 257/98, E51.022, E51.026; 438/82, 99
See application file for complete search history.

(56) References Cited

U.S. PATENT DOCUMENTS

| 5,141,671 A | 8/1992 | Bryan et al. |
| 6,500,885 B1 * | 12/2002 | Porter et al. ................ 524/94 |
| 6,579,630 B2 | 6/2003 | Li et al. |

(Continued)

FOREIGN PATENT DOCUMENTS

EP    0 579 151 A2    1/1994

(Continued)

OTHER PUBLICATIONS

Form PCT/IB/338 mailed Mar. 12, 2009 from PCT/JP2007/066639 plus attached Forms PCT/IB/373, PCTISA/237, PCT/IB/326, and PCT/IB/373.

(Continued)

*Primary Examiner* — Phuc T Dang
(74) *Attorney, Agent, or Firm* — Birch Stewart Kolasch Birch, LLP

(57) ABSTRACT

Disclosed is an organic electroluminescent device (organic EL device) that utilizes phosphorescence and is improved in luminous efficiency and fully secured of driving stability. The organic EL device comprises an anode, an organic layer containing a hole-transporting layer, a light-emitting layer, and an electron-transporting layer, and a cathode piled one upon another on a substrate while the hole-transporting layer is disposed between the light-emitting layer and the anode and the electron-transporting layer is disposed between the light-emitting layer and the cathode. The light-emitting layer comprises an aluminum heterocomplex or dimeric complex of deuterated substituted or unsubstituted 2-methyl-8-hydroxyquinoline (Me8HQ-D) in which the hydrogen atoms in the methyl group of substituted or unsubstituted 2-methyl-8-hydroxyquinoline (Me8HQ) are deuterated as a host material and an organic metal complex containing at least one metal selected from groups 7 to 11 of the periodic table as a guest material.

6 Claims, 7 Drawing Sheets

U.S. PATENT DOCUMENTS

| | | | |
|---|---|---|---|
| 6,905,904 B2 * | 6/2005 | Gardner et al. | 438/31 |
| 7,456,317 B2 * | 11/2008 | Gant et al. | 564/305 |
| 2007/0054148 A1 | 3/2007 | Matsuo et al. | |

FOREIGN PATENT DOCUMENTS

| | | |
|---|---|---|
| JP | 5-214332 A | 1/1993 |
| JP | 5-198377 A | 8/1993 |
| JP | 6-172751 A | 6/1994 |
| JP | 2003-142264 A | 5/2003 |
| JP | 2004-515506 A | 5/2004 |
| WO | WO-2005/014551 A1 | 2/2005 |

OTHER PUBLICATIONS

C. C. Tong, "Enhancement of OLED Efficiencies and High-Voltage Stabilities of Light-Emitting Materials by Deuteration," J. Phys. Chem. C., 2007, vol. 111, pp. 3490-3494.

European Search Report issued Oct. 5, 2010, in European Patent Application No. 07793079.0.

* cited by examiner

US 7,968,874 B2

ORGANIC ELECTROLUMINESCENT DEVICE MATERIAL AND ORGANIC ELECTROLUMINESCENT DEVICE

CROSS-REFERENCE TO RELATED APPLICATION

This application is a 371 of PCT/JP2007/066639 filed Aug. 28, 2007.

FIELD OF TECHNOLOGY

This invention relates to an organic electroluminescent device (hereinafter referred to as organic EL device) and an organic electroluminescent device material (hereinafter referred to as organic EL device material or organic EL material) and, more particularly, to a thin-film device that emits light when an electrical field is applied to its light-emitting layer constituted of organic compounds.

BACKGROUND TECHNOLOGY

In the development of electroluminescent devices utilizing organic materials, optimization of the kind of electrodes for the purpose of improving the charge-injecting efficiency from the electrodes and disposition of a hole-transporting layer of an aromatic diamine and a light-emitting layer of 8-hydroxyquinoline aluminum complex (hereinafter referred to as Alq3) in thin film between the electrodes have created a device with a remarkable improvement in luminous efficiency over the conventional devices that utilize single crystals of anthracene and the like. Following this, the developmental works of organic EL devices have been focused on their applications to high-performance flat panels characterized by self-luminescence and high-speed response.

In an attempt to improve the luminous efficiency of such organic EL devices still further, modifications of the aforementioned basic structure of anode/hole-transporting layer/light-emitting layer/cathode by suitable addition of a hole-injecting layer, an electron-injecting layer, or an electron-transporting layer have been found effective for enhancing the luminous efficiency and a large number of organic materials conforming to the function of these layered structures have been developed.

In another attempt to enhance the luminous efficiency of an organic EL device, the use of phosphorescence in place of fluorescence has been investigated. The aforementioned device comprising an aromatic diamine in the hole-transporting layer and Alq3 in the light-emitting layer and many other devices utilize fluorescence. Now, the utilization of phosphorescence, that is, emission of light from the excited triplet state, is expected to enhance the luminous efficiency approximately three times that of the conventional devices utilizing fluorescence (singlet). The prior documents relating to this invention are listed below.

Patent document 1: WO00/70655
Patent document 2: JP2001-284056A
Patent document 3: JP5-198377A
Patent document 4: JP2003-142264A
Patent document 5: WO2002/47440
Patent document 6: WO001/041512
Patent document 7: JP2001-313178A
Patent document 8: JP2002.305083A
Patent document 9: JP5.214332A
Non-patent document 1: Appl. Phys. Lett., Vol. 77, p 904 (2000)

Reports are published in recent years on the possibility of enhancing the luminous efficiency in phosphorescent electroluminescence by doping the light-emitting layer with an iridium complex as a guest material and a number of disclosures are made in the patent documents 1 and 6 and elsewhere. A typical example is tris(2-phenylpyridine)iridium complex (hereinafter referred to as Ir(ppy)3) which is a phosphorescent material emitting green light. It has been found that iridium complexes are made to emit light in a wide wavelength range from blue to red by changing the chemical structure of the ligands.

The use of 4,4'-bis(9-carbazolyl)biphenyl (hereinafter referred to as CBP) as a host material in the light-emitting layer of an organic EL device is proposed in the patent documents 1 and 7. However, CBP has a specific property of facilitating the flow of holes and obstructing the flow of electrons and CBP used as a host material for Ir(ppy)3 destroys the balanced injection of electrical charges thereby causing excess holes to flow out to the side of the electron-transporting layer. As a result, the luminous efficiency from Ir(ppy)3 drops.

One of the means to solve the aforementioned problems is providing a hole-blocking layer between the light-emitting layer and the electron-transporting layer as described in the patent documents 2 and 8. The hole-blocking layer can attain the object of enhancing the luminous efficiency by accumulating holes effectively in the light-emitting layer and improving the probability of recombination of holes with electrons in the light-emitting layer. The hole-blocking materials in general use include 2,9-dimethyl-4,7-diphenyl-1,10-phenanthroline (hereinafter referred to as BCP) and p-phenylphenolato-bis(2-methyl-8-quinolinolato-N1,O8)aluminum (hereinafter referred to as BAlq). The hole-blocking layer thus provided can prevent electrons and holes from recombining in the electron-transporting layer. However, a device utilizing BCP shows an extremely short life as BCP tends to crystallize easily even at room temperature and lacks reliability as a hole-blocking material. On the other hand, BAlq has an insufficient ability to block holes and causes a drop in the luminous efficiency from Ir(ppy)3, although it is reported to show a relatively satisfactory life. Moreover, providing the hole-blocking layer means adding one more layer which complicates the structure of a device and increases the cost.

On the other hand, the use of the aforementioned BCP and 3-phenyl-4-(1'-naphthyl)-5-phenyl-1,2,4-triazole (hereinafter referred to as TAZ) as a host material in phosphorescent organic EL devices is proposed; however, the cited compounds have a specific property of facilitating the flow of electrons and obstructing the flow of holes and their use as a host material shifts the light-emitting range toward the side of the hole-transporting layer. Therefore, there may arise a problem of the luminous efficiency from Ir(ppy)3 dropping depending upon the compatibility of Ir(ppy)3 with the material chosen for the hole-transporting layer. For example, 4,4'-bis[N-(1-naphthyl)-N-phenylamino]biphenyl (hereinafter referred to as α-NPD) is used most widely as a material for the hole-transporting layer on account of its good performance, high reliability, and long life; however, the use of α-NPD together with Ir(ppy)3 causes transition of energy from Ir(ppy)3 to α-NPD and results in a drop of the luminous efficiency.

A BAlq-containing luminescent composition emitting blue light is disclosed in the patent document 9. As is apparent here, BAlq and related compounds are used not only as light-emitting materials but also as materials for other layers.

It is reported in the non-patent document 1 that light can be emitted at high efficiency from a phosphorescent electroluminescent device of three-layer structure constituted of a light-emitting layer containing TAZ or the like as a host material and Ir(ppy)3 as a guest material, an electron-transporting layer containing Alq3, and a hole-transporting layer containing 4,4'-bis[N,N'-(3-toluyl)amino]-3,3'-dimethylbiphenyl (hereinafter referred to as HMTPD). However, HMTPD tends to crystallize easily as its glass transition temperature (hereinafter referred to as Tg) is approximately 50° C. and lacks reliability as a hole-transporting material. In consequence, a device of the aforementioned structure encounters problems in that it shows an extremely short life, it is not readily applicable commercially, and it requires high driving voltage.

The patent document 3 discloses the incorporation of a dimeric metal complex containing an 8-quinolinol ligand represented by $Q_2$-Al—O—Al-$Q_2$ in the blue light-emitting layer and the use of this complex together with a fluorescent colorant such as perylene and the patent document 4 discloses the use of a dimeric metal complex as a phosphorescent host material; however, these patent documents do not teach the usefulness of a deuterated dimeric metal complex. Here, the dimeric metal complex refers to a metal complex having a structure represented by $Q_2$-Al—O—Al-$Q_2$ wherein Q is a substituted or unsubstituted 8-quinolinol ligand.

Isotopic atoms such as $^2$H (termed heavy hydrogen or D) and $^{13}$C have been utilized widely for labeling with isotope tracers in medical treatment and structural analysis of compounds. In connection with the organic EL field, the patent document 5 discloses that the carbon-deuterium (C-D) bond is shorter than the carbon-hydrogen (C—H) bond and the former is more stable physicochemically than the latter and cites a variety of deuterated compounds (designated as compound-D).

Hetero ligand metal complexes and dimeric metal complexes such as BAlq are useful as organic EL materials; however, none of the documents teaches the necessity or effectiveness of replacing hydrogen atoms in the methyl group at position 2 (benzylic hydrogen) in the quinolinol ligand with deuterium atoms.

DISCLOSURE OF THE INVENTION

Problems to be Solved by the Invention

In application of organic EL devices to display devices such as flat panel displays, it is necessary to improve the luminous efficiency of the device and, at the same time, to fully secure the driving stability. In view of the aforementioned circumstances, an object of this invention is to provide an organic EL device of practical usefulness that performs at high efficiency, shows a long life, and can be fabricated in a simplified structure and a material useful therefor.

Means to Solve the Problems

The inventors of this invention have conducted intensive studies, found that the use of a hetero ligand metal complex or dimeric metal complex having a quinolinol ligand in which Hs in the methyl group at position 2 are replaced with Ds as an organic EL device material can solve the aforementioned problems, and completed this invention.

The benzylic hydrogen atoms in the methyl group at position 2 in the quinolinol ligand of a hetero ligand metal complex or dimeric metal complex are highly reactive and unstable, but this methyl group cannot be omitted structurally as its steric hindrance controls the number of ligands bound to the aluminum metal. Conversion of the methyl group to another substituent of low reactivity such as a phenyl group brings about changes in the optical and other physicochemical properties of the metal complex. The inventors of this invention have found that selective deuteration of the benzylic hydrogen atoms with physicochemically stable deuterium atoms protects the methyl group and increases its stability without changing the properties of the material, and completed this invention.

This invention relates to an organic electroluminescent device material comprising an organic metal complex represented by the following general formula (I):

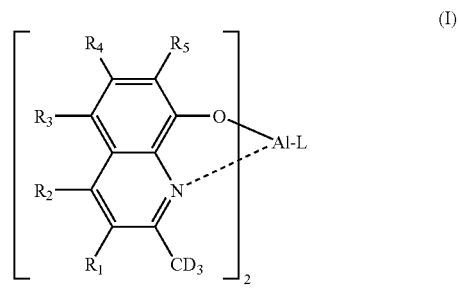

(I)

wherein, $R_1$ to $R_5$ each is independently a monovalent substituent selected from hydrogen atoms, deuterium atoms, alkyl groups, aralkyl groups, alkenyl groups, a cyano group, alkoxy groups, substituted or unsubstituted aromatic hydrocarbon groups, and substituted or unsubstituted aromatic heterocyclic groups; when the monovalent substituent has hydrogen atoms, the hydrogen atoms may be deuterium atoms; D is a deuterium atom; L is a monovalent group represented by the following formula (1), (2), (3), or (4)

(1)

(2)

(3)

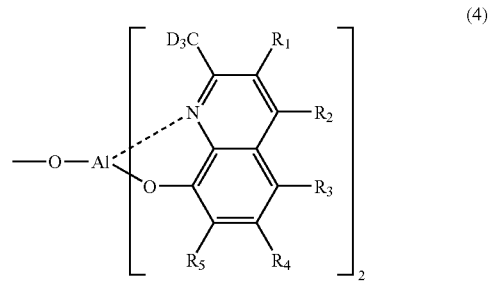

(4)

in which $Ar_1$ to $Ar_5$ each is independently a substituted or unsubstituted aromatic hydrocarbon group or a substituted or unsubstituted aromatic heterocyclic group, Z is silicon or germanium, and $R_1$ to $R_5$ and D are as defined above.

Of the organic metal complexes represented by general formula (I), preferable are those represented by the following general formula (II) or (III).

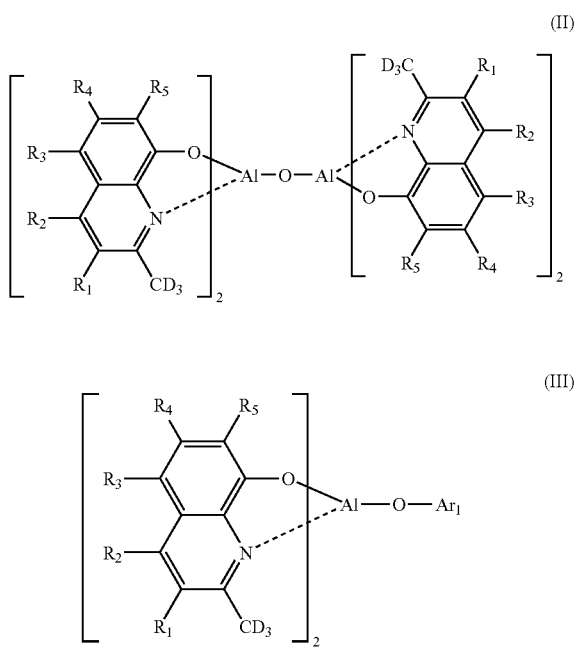

wherein, $R_1$ to $R_5$ and D are as defined in general formula (I) and $Ar_1$ is as defined in formula (1), preferably an aromatic hydrocarbon group of 1 to 3 rings.

An organic electroluminescent device according to this invention comprises an anode, an organic layer containing a hole-transporting layer, a light-emitting layer, and an electron-transporting layer, and a cathode piled one upon another on a substrate and at least one of the layers in the organic layer contains the aforementioned organic electroluminescent device material.

Advantageously, the organic electroluminescent device comprises an anode, an organic layer containing a hole-transporting layer, a light-emitting layer, and an electron-transporting layer, and a cathode piled one upon another on a substrate, while the hole-transporting layer is disposed between the light-emitting layer and the anode, the electron-transporting layer is disposed between the light-emitting layer and the cathode, and the aforementioned organic electroluminescent device material is incorporated in the light-emitting layer. More advantageously, the organic electroluminescent device comprises the aforementioned organic electroluminescent device material in the light-emitting layer as a host material and an organic metal complex having at least one metal selected from groups 7 to 11 of the periodic table as a guest material.

Preferably, the organic electroluminescent device has a hole-injecting layer disposed between the anode and the hole-transporting layer or an electron-injecting layer disposed between the cathode and the electron-transporting layer.

An organic electroluminescent device material (organic EL material) according to this invention is an organic metal complex represented by the aforementioned general formula (I). Such organic metal complexes in which D is replaced with H are known in the aforementioned patent documents 4, 8, and 9. Hence, these documents help one understand what the groups such as $R_1$ and L in the aforementioned general formula (I) mean and what groups are preferable.

In general formula (I), $R_1$ to $R_5$ each is independently a hydrogen atom, a deuterium atom, or a monovalent substituent. The monovalent substituent is selected from alkyl groups, aralkyl groups, alkenyl groups, a cyano group, alkoxy groups, substituted or unsubstituted aromatic hydrocarbon groups, and substituted or unsubstituted aromatic heterocyclic groups. Where the monovalent substituent has hydrogen atoms, the hydrogen atoms may be deuterium atoms. Where the substituent group of interest is a methyl group, it is preferably $CD_3$.

Preferably, the alkyl groups include alkyl groups of 1 to 6 carbon atoms (hereinafter referred to as lower alkyl groups), the aralkyl groups include a benzyl group and a phenetyl group, the alkenyl groups include lower alkenyl groups of 1 to 6 carbon atoms, and the alkoxy groups include those having a lower alkyl moiety.

Further, the aromatic hydrocarbon groups include a phenyl group, a naphthyl group, an acenaphthyl group, and an anthryl group and the aromatic heterocyclic groups include a pyridyl group, a quinolyl group, a thienyl group, a carbazolyl group, an indolyl group, and a furyl group. Where the aforementioned aromatic hydrocarbon groups or aromatic heterocyclic groups have substituents, such substituents include lower alkyl groups, lower alkoxy groups, a phenoxy group, a benzyloxy group, a phenyl group, and a naphthyl group.

The group L is a monovalent group represented by the aforementioned formula (1), (2), (3), or (4) in which $Ar_1$ to $Ar_5$ each is independently a substituted or unsubstituted aromatic hydrocarbon group or a substituted or unsubstituted aromatic heterocyclic group and Z is silicon or germanium. Examples of the substituted or unsubstituted aromatic hydrocarbon group or substituted or unsubstituted aromatic heterocyclic group here are the same as those cited above.

Of the organic metal complexes represented by general formula (I), preferable are those which are selected from complexes represented by general formula (I) in which $Ar_1$ to $Ar_5$ each is a hydrogen atom, a lower alkyl group, or a lower alkoxy group. The hydrogen atoms in the lower alkyl group or lower alkoxy group here may be D. In formulas (1) to (3), $Ar_1$, $Ar_2$, and $Ar_3$ each is preferably an aromatic hydrocarbon group of 1 to 3 rings. Furthermore, L is preferably selected from aryloxy groups such as phenoxy, phenylphenoxy, naphthoxy, phenylnaphthoxy, and naphthylphenoxy and monovalent groups represented by formula (4). Where L is a monovalent group represented by formula (4), the resulting organic metal complex is represented by general formula (II).

The organic metal complex represented by general formula (I) is synthesized by a complex-forming reaction from a salt of the metal salt and a 2:1 mixture of a compound represented by formula (IV) and a compound represented by formula (1a), (2a), or (3a) on a molar basis. The organic metal complex represented by general formula (II) is synthesized by a complex-forming reaction from a salt of the metal salt and a compound represented by formula (IV). The groups $R_1$ to $R_5$ in formula (IV) respectively correspond to $R_1$ to $R_5$ in general formula (I). The compound represented by formula (1a), (2a), or (3a) yields the monovalent group represented by the aforementioned formula (1), (2), or (3) and $R_1$ to $R_5$ and Z in formula (1), (2), or (3) correspond to $R_1$ to $R_5$ and Z in formula (1a), (2a), or (3a).

The organic metal complex represented by general formula (II) can be synthesized, for example, in accordance with the method described by Y. Kushi and coworkers [J. Amer. Chem. Soc., Vol. 92, p 91 (1970)]. The groups $R_1$ to $R_5$ in general formula (II) correspond to $R_1$ to $R_5$ in general formula (I). The metal salts include $AlCl_3$ and $Al(Oi-Pr)_3$.

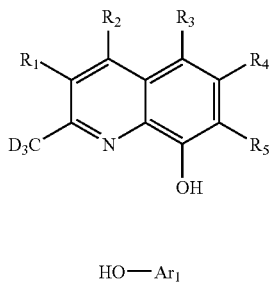 (IV)

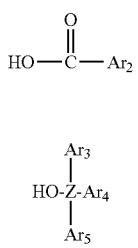 (1a)

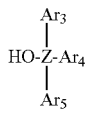 (2a)

(3a)

$$\begin{matrix} & Ar_3 \\ HO-Z-Ar_4 \\ & Ar_5 \end{matrix}$$

The compound represented by formula (IV) can be obtained from 2-methyl-8-hydroxyquinoline (Me8HQ) by replacing the hydrogen atoms of the methyl group with deuterium atoms. The compound obtained in this manner in which the hydrogen atoms of the methyl group of Me8HQ are replaced with deuterium atoms is referred to as Me8HQ-D. The deuteration reaction can be carried out under known conditions. For example, the hydrogen atoms in the methyl group can be selectively deuterated by reacting Me8HQ with heavy water in the presence of a Pd/C catalyst at 150 to 200° C. In the case where any of $R_1$ to $R_5$ in general formula (I) is a hydrogen atom or an alkyl group having a free hydrogen atom, the hydrogen atom may also be partially deuterated depending upon the reaction conditions, but this outcome produces no ill effects. The degree of deuteration of the hydrogen atoms in the methyl group at position 2 is controlled at 40% or more, preferably 90% or more, more preferably 95% or more. Therefore, according to this invention, the methyl group at position 2 of an organic metal complex represented by general formula (I) is primarily $CD_3$ and may contain a small amount of $CD_2H$, $CDH_2$, or $CH_3$.

Examples of the organic EL materials comprising the organic metal complexes represented by general formula (I) are shown below, but the organic EL materials useful for this invention are not limited to these compounds.

(Compound 1)

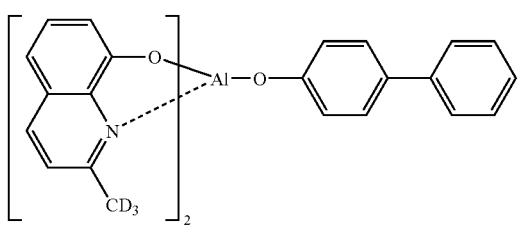

(Compound 2)

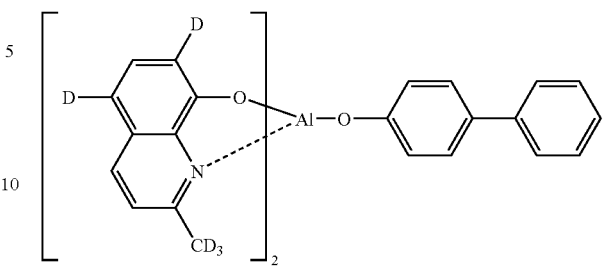

(Compound 3)

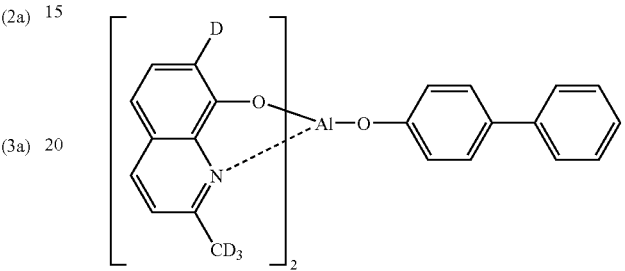

(Compound 4)

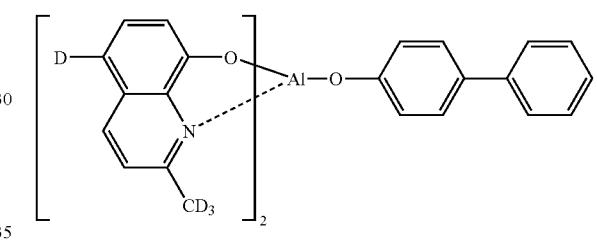

(Compound 5)

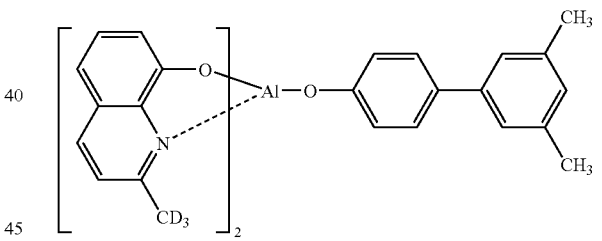

(Compound 6)

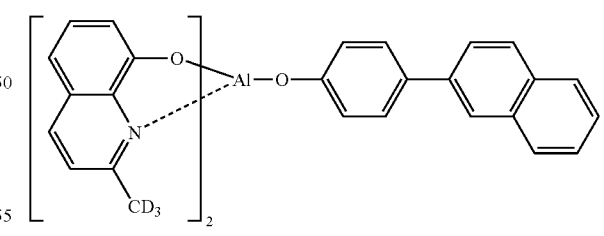

(Compound 7)

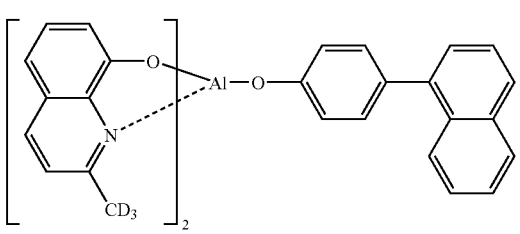

(Compound 8)
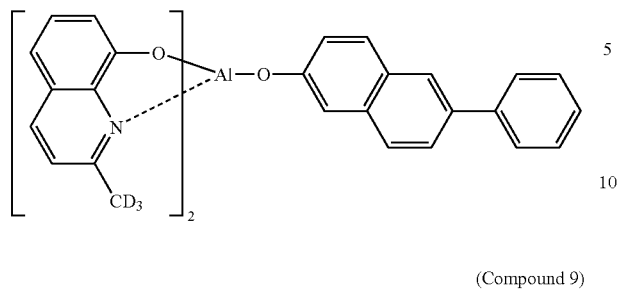
(Compound 9)
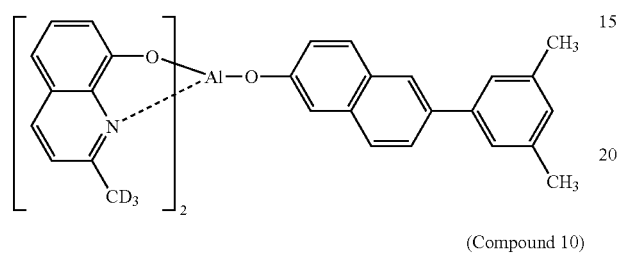
(Compound 10)
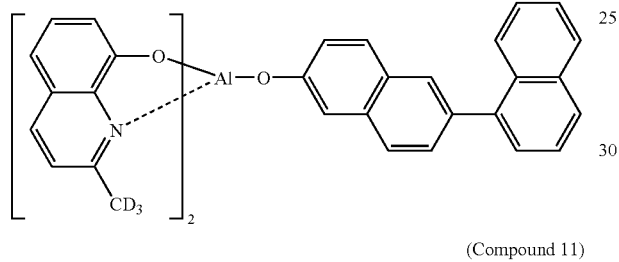
(Compound 11)
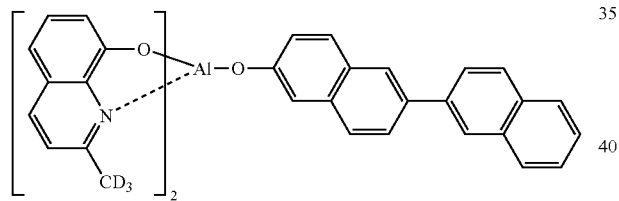
(Compound 12)
(Compound 13)
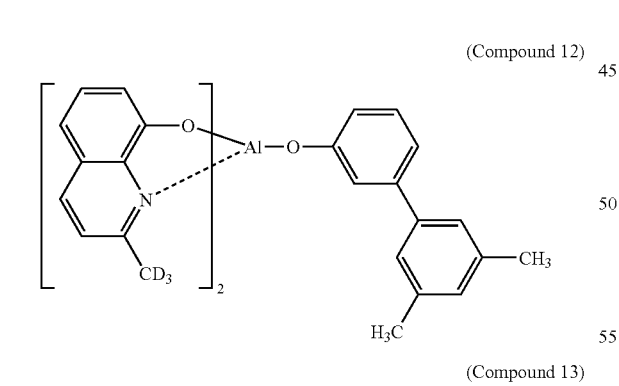
(Compound 14)
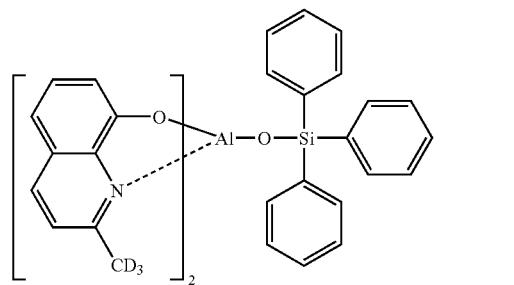
(Compound 15)
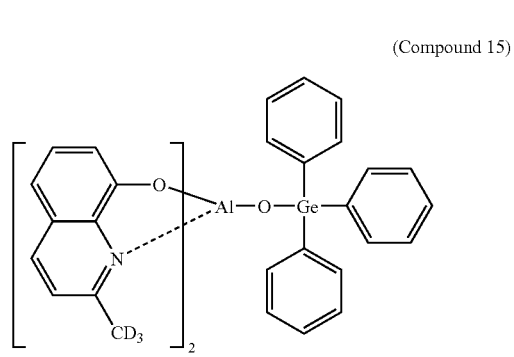
(Compound 21)
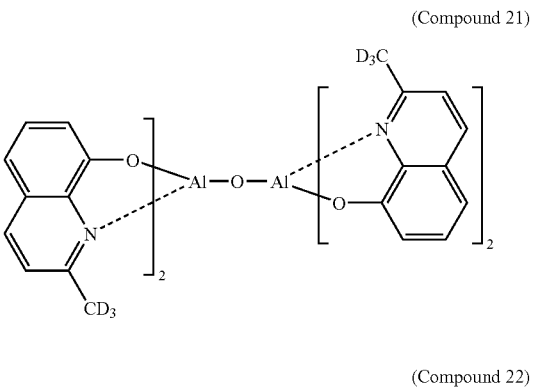
(Compound 22)
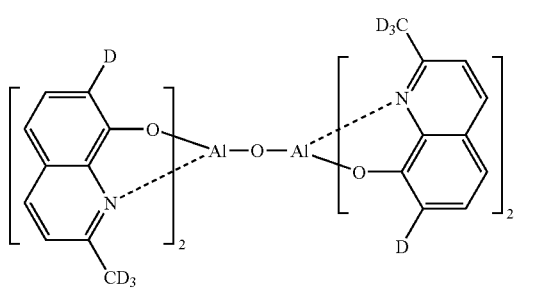
(Compound 23)
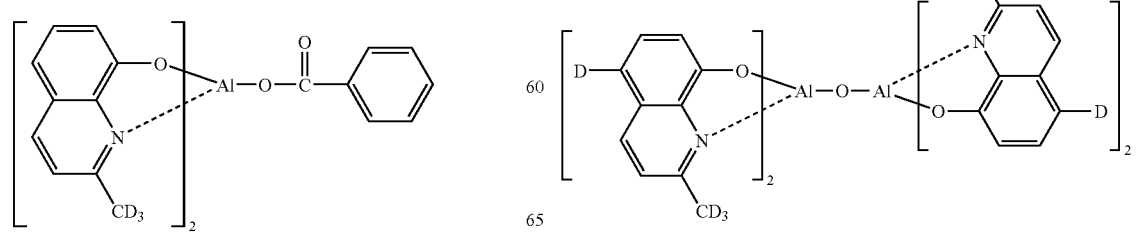

(Compound 24)
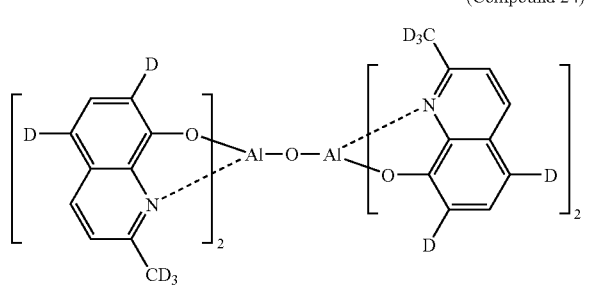

(Compound 25)
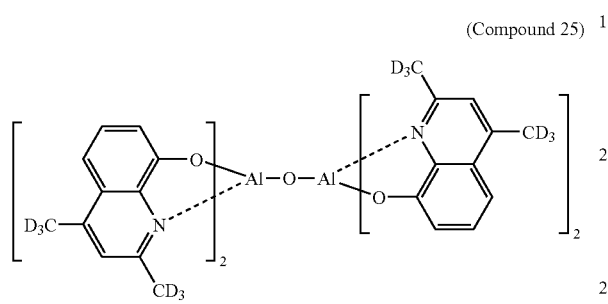

(Compound 26)
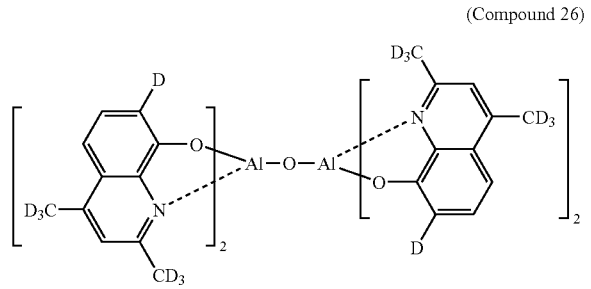

(Compound 27)
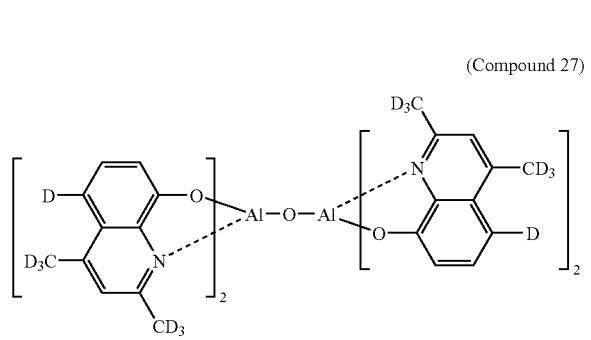

(Compound 28)
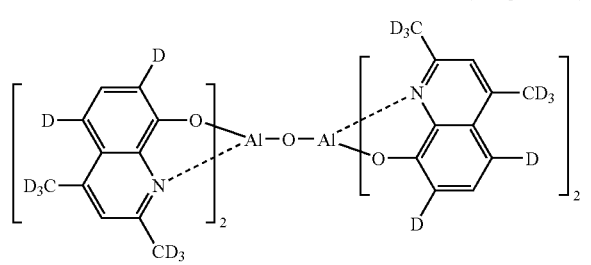

(Compound 29)
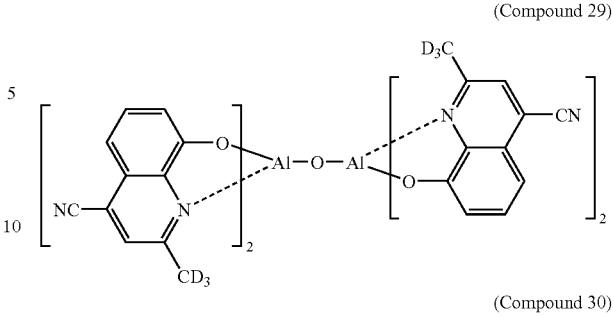

(Compound 30)
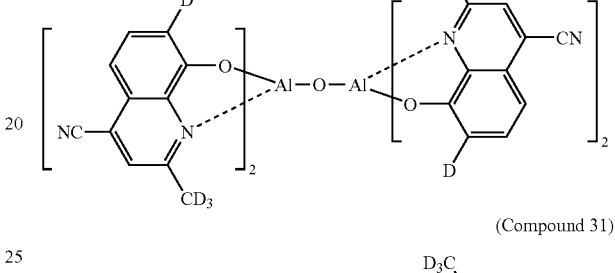

(Compound 31)
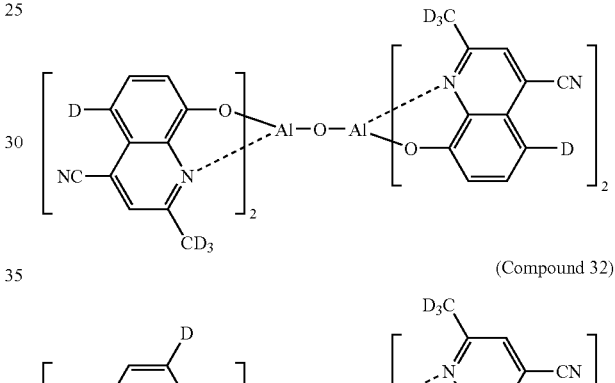

(Compound 32)
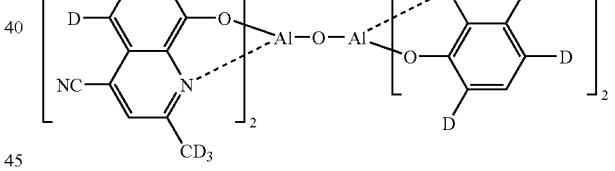

An organic EL device provided by this invention comprises at least one layer of an organic EL material comprising an organic metal complex represented by general formula (I) in its organic layer. The organic EL device has a structure constructed by piling an anode, an organic layer containing a hole-transporting layer, a light-emitting layer and an electron-transporting layer, and a cathode one upon another; preferably, the anode, the organic layer containing the hole-transporting layer, the light-emitting layer, and the electron-transporting layer, and the cathode are piled one upon another on a substrate while the hole-transporting layer is disposed between the anode and the light-emitting layer and the electron-transporting layer is disposed between the light-emitting layer and the cathode. A more advantageous structure has a hole-injecting layer disposed between the anode and the hole-transporting layer or an electron-injecting layer disposed between the cathode and the electron-transporting layer.

The light-emitting layer preferably comprises the organic EL material as a light-emitting material. Advantageously, the light-emitting layer comprises the organic EL material as a host material and an organic metal complex containing at least one metal selected from groups 7 to 11 of the periodic table as a guest material. However, the organic EL material may be used as a material for other organic layers, for example, as a hole-blocking material.

A device comprising the organic EL material as a host material and another material as a guest material in its light-emitting layer constitutes a phosphorescent organic EL device. Here, the host material means a material that accounts for 50 wt % or more of the materials constituting the layer of interest while the guest material accounts for less than 50 wt %. According to this invention, the organic EL material incorporated in the light-emitting layer of the organic EL device is fundamentally required to have an energy level of excited triplet state higher than that of the phosphorescent organic metal complex incorporated in the same layer The host material is required to be a compound that can form a thin film of stable shape or has a high Tg and is capable of transporting holes or electrons efficiently. Further, it is required to be a compound that is electrochemically and chemically stable and generates with difficulty impurities that become traps or quench the light either during fabrication or use. It is also important that the host material must have such a hole-injecting ability as to maintain the light-emitting range at a suitable distance from the interface of the hole-transporting layer thereby permitting the phosphorescent organic metal complex to emit light with the least influence from the excited triplet level of the hole-transporting layer.

The guest material is preferably an organic metal complex containing a metal of 7 to 11 groups of the periodic table. More preferably, such an organic metal complex contains a metal selected from iridium, osmium, rhodium, palladium, and platinum. Of these metals, iridium, rhodium, and platinum are preferable and iridium is most preferable.

The guest materials useful for this invention generally include the compounds described in the aforementioned patent documents, but are not limited to them.

Concrete examples of the guest materials are shown below, but the useful guest materials are not limited to these compounds. One of the synthetic methods applicable to these compounds is described in Inorg. Chem., Vol. 40, pp 1704-1711.

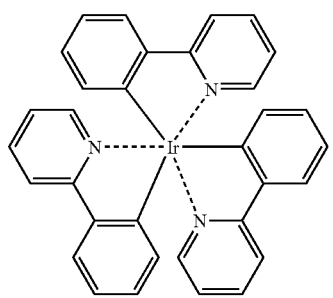

(Compound 41)

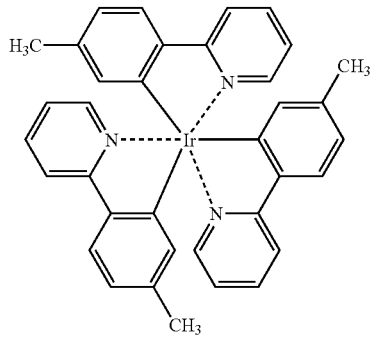

(Compound 42)

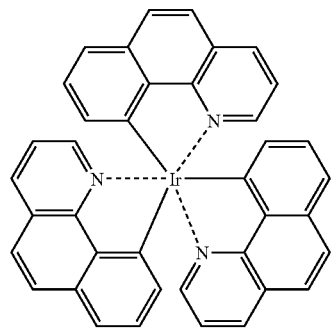

(Compound 43)

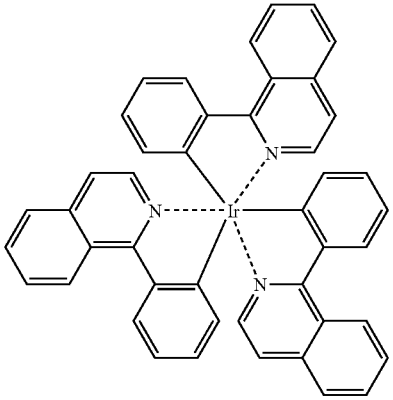

(Compound 44)

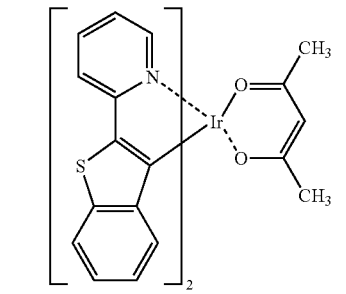

(Compound 45)

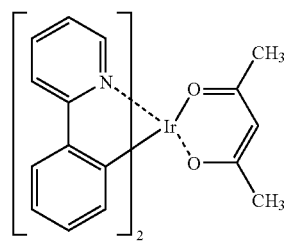

(Compound 46)

-continued (Compound 47)

[chemical structure]

EXPLANATION OF SYMBOLS

1, substrate; 2, anode; 3, hole-injecting layer; 4, hole-transporting layer; 5, light-emitting layer; 6, electron-transporting layer; 7, cathode.

PREFERRED EMBODIMENTS OF THE INVENTION

Figure 1:
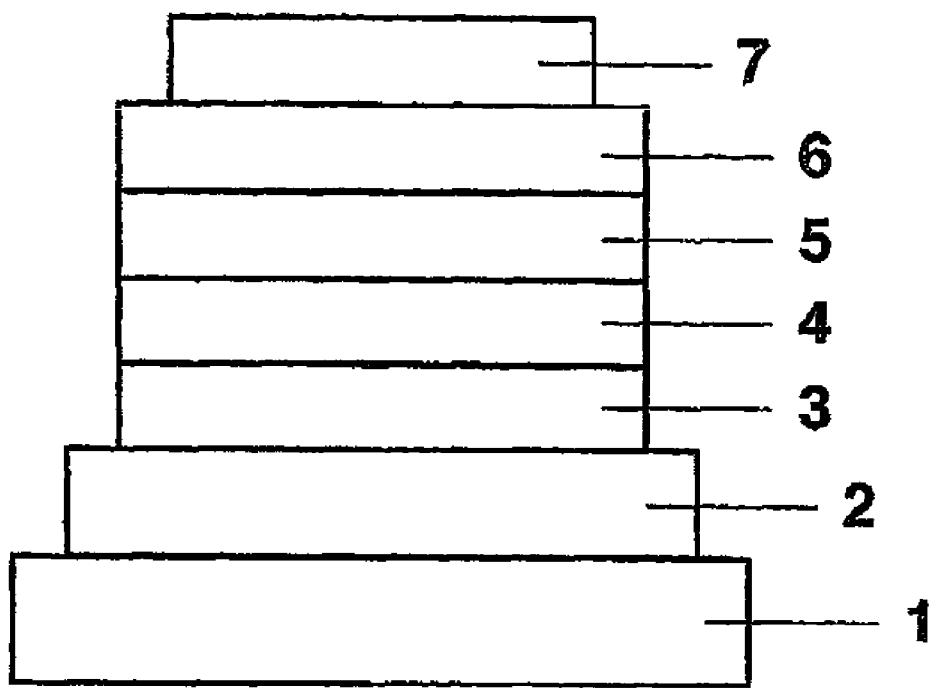
FIG. 1 schematically shows the cross section of an example of organic electroluminescent device.

An organic EL device to be provided by this invention is explained below with reference to the drawing. FIG. 1 is the cross section schematically illustrating a general structure of an organic El device to be used in this invention. The organic EL device comprises a substrate, an anode, a hole-transporting layer, a light-emitting layer, an electron-transporting layer, and a cathode as essential layers and non-essential layers, for example, a hole-blocking layer, may be omitted or, as needed, other non-essential layers may be added. Omission of the hole-blocking layer may offer an advantage in that the layered structure can be simplified.

The substrate 1 serves as a support of the organic electroluminescent device and is made from a quartz or glass plate, a metal plate or foil, or a plastic film or sheet. In particular, a transparent sheet of synthetic resin such as polyester, polymethacrylate, polycarbonate, and polysulfone is preferable. When a synthetic resin is used for the substrate, it is necessary to take the gas barrier property of the resin into consideration. If the gas barrier property of the substrate were too poor, the air would undesirably pass through the substrate to degrade the organic electroluminescent device. One of the preferable methods to secure the necessary gas barrier property is to provide a dense silicon oxide film on at least one side of the synthetic resin substrate.

The anode 2 is provided on the substrate 1 and plays a role of injecting holes into the hole-transporting layer. The anode is usually constructed of a metal such as aluminum, gold, silver, nickel, palladium, and platinum, a metal oxide such as oxide of indium and/or tin, a metal halide such as copper iodide, carbon black, or an electrically conductive polymer such as poly(3-methylthiophene), polypyrrole, and polyaniline. The anode is usually formed by a technique such as sputtering and vacuum deposition. When silver or any other suitable metal, copper iodide, carbon black, an electrically conductive metal oxide, or an electrically conductive polymer is available in the form of fine particles, the anode 2 can be formed by dispersing the particles in a solution of a suitable binder resin and coating the substrate 1 with the dispersion. Furthermore, in the case of an electrically conductive polymer, the anode 2 may be formed by electrolytically polymerizing the corresponding monomer to form a thin film of the polymer directly on the substrate 1 or by coating the substrate 1 with the electrically conductive polymer. The anode may also be formed by piling different materials one upon another. The anode varies in thickness with the requirement for transparency. Where transparency is required, the transmittance of visible light is usually kept at 60% or more, preferably at 80% or more. In this case, the thickness becomes usually 5 to 1000 nm, preferably 10 to 500 nm. Where opaqueness is acceptable, the anode 2 may be the same in the transmittance as the substrate 1. Further, a different electrically conductive material can be piled on the aforementioned anode 2.

The hole-transporting layer 4 is provided on the anode 2. It is allowable to dispose the hole-injecting layer 3 between the anode and the hole-transporting layer. A material for the hole-transporting layer is required to be capable of injecting holes from the anode at high efficiency and transporting the injected holes efficiently. To attain this objective, the material must satisfy the following requirements: it has a low ionization potential, it is highly transparent against visible light, it shows a high hole mobility, it is highly stable, and it generates with difficulty impurities that become traps during fabrication or use. Still more, since the hole-transporting layer is arranged in contact with the light-emitting layer, the material for the hole-transporting layer must not quench the light from the light-emitting layer nor form exciplexes with the light-emitting layer to lower the luminous efficiency. Besides the aforementioned general requirements, heat resistance is further required when application of the device to vehicle displays is considered. Hence, the material preferably has a Tg of 85° C. or above. A known triarylamine dimer such as α-NPD is used preferably as a hole-transporting material.

The triarylamine dimer may be used together with other compounds that are known as hole-transporting materials, if necessary. For example, such other compounds include aromatic diamines containing two tertiary amines whose nitrogen atoms are substituted with 2 or more condensed aromatic groups, aromatic amines of a starburst structure such as 4,4', 4"-tris(1-naphthylphenylamino)triphenylamine, an aromatic amine consisting of a tetramer of triphenylamine, and Spiro compounds such as 2,2',7,7'-tetrakis-(diphenylamino)-9,9'-spirobifluorene. These compounds may be used singly or, if necessary, as a mixture. In addition to the aforementioned compounds, the materials useful for the hole-transporting layer include polymeric materials such as polyvinylcarbazole, polyvinyltriphenylamine, and polyaryleneethersulfones containing tetraphenylbenzidine.

When the coating process is used for forming the hole-transporting layer, a coating solution prepared from one kind or more of hole-transporting materials and, if necessary, binder resins that do not become a trap of holes and additives such as an improver of coating properties is applied to the anode 2 by a process such as spin coating and dried to form the hole-transporting layer 4. Examples of the binder resins are polycarbonate, polyarylate, and polyester. Since a binder resin lowers the hole mobility when added in a large amount, its addition is preferably kept at a low level, usually below 50 wt %.

When the vacuum deposition process is used for forming the hole-transporting layer, the selected hole-transporting material is introduced to a crucible placed in a vacuum container, the container is evacuated to $1 \times 10^{-4}$ Pa or so by a suitable vacuum pump, the crucible is heated to evaporate the hole-transporting material, and the vapor is deposited on the substrate that has the anode formed thereon and is placed opposite the crucible to form the hole-transporting layer 4. The thickness of the hole-transporting layer 4 is normally 5 to 300 nm, preferably 10 to 100 nm. The vacuum deposition process is generally used to form a thin film such as this uniformly.

The light-emitting layer 5 is provided on the hole-transporting layer 4. The light-emitting layer 5 comprises one kind or more of the organic metal complexes represented by the aforementioned general formula (I) and the aforementioned guest material (for example, an Ir complex); on application of an electrical field between the electrodes, the holes that are injected from the anode and migrating through the hole-transporting layer and the electrons that are injected from the cathode and migrating through the electron-transporting layer 6 recombine to excite the light-emitting layer thereby causing emission of intense light The light-emitting layer 5 may contain other components, for example, other host materials (functioning similarly to organic metal complexes represented by general formula (I)) and fluorescent colorants to the extent that they do not damage the performance stipulated by this invention.

The content of the guest material in the light-emitting layer is preferably in the range of 0.1 to 30 wt %. A content of less than 0.1 wt % does not contribute to improve the luminous efficiency of the device while a content in excess of 30 wt % causes concentration quenching due to dimerization of organic metal complexes and a resultant drop in luminous efficiency. In the conventional devices utilizing fluorescence (singlet), a desirable tendency is observed when the guest material is somewhat larger in amount than the fluorescent colorant (dopant) in the light-emitting layer. The guest material may be incorporated partially or distributed nonuniformly in the direction of film thickness.

The thickness of the light-emitting layer 5 is normally 10 to 200 nm, preferably 20 to 100 nm. The light-emitting layer is formed in thin film in the same manner as for the hole-transporting layer 4.

To improve the luminous efficiency of the device still further, the electron-transporting layer 6 is disposed between the light-emitting layer 5 and the cathode 7. The electron-transporting layer 6 is formed from a compound that can transport the electrons injected from the cathode toward the light-emitting layer 5 efficiently when an electrical field is applied between the electrodes. An electron-transporting compound useful for the electron-transporting layer 6 must inject electrons from the cathode 7 at high efficiency, have a high electron mobility, and transport the injected electrons efficiently.

The electron-transporting materials satisfying these requirements include metal complexes such as Alq3, 10-hydroxybenzo[h]quinoline metal complexes, oxadiazole derivatives, distyrylbiphenyl derivatives, silole derivatives, 3- or 5-hydroxyflavone metal complexes, benzoxazole metal complexes, benzothiazole metal complexes, trisbenzimidazolylbenzene, quinoxaline compounds, phenanthroline derivatives, 2-t-butyl-9,10-N,N'-dicyanoanthraquinonediimine, n-type hydrogenated amorphous silicon carbide, n-type zinc sulfide, and n-type zinc selenide. The thickness of the electron-transporting layer 6 is normally 5 to 200 nm, preferably 10 to 100 nm. The electron-transporting layer 6 is formed on the light-emitting layer 5 by a process such as coating and vacuum deposition as in the formation of the hole-transporting layer 4. The vacuum deposition process is normally used.

To enhance still further the hole-injecting efficiency and improve the adhesive strength of the organic layer as a whole to the anode, the hole-injecting layer 3 is disposed between the hole-transporting layer 4 and the anode 2 at times. Disposition of the hole-injecting layer 3 produces an effect of lowering the driving voltage of the device in the initial period and, at the same time, suppressing a rise in voltage during continuous driving of the device at constant current density. A material for the hole-injecting layer is required to adhere closely to the anode, form a thin film uniformly, and show good thermal stability; that is, the material is required to have a melting point of 300° C. or above and a glass transition temperature of 100° C. or above. Still more, the material desirably has a low ionization potential to facilitate injection of holes from the anode and a high hole mobility.

The materials that have been reported as attaining the aforementioned object include phthalocyanine compounds such as copper phthalocyanine, organic compounds such as polyaniline and polythiophene, sputtered carbon membranes, and metal oxides such as vanadium oxide, ruthenium oxide, and molybdenum oxide. The hole-injecting layer can be formed in thin film as in the case of the hole-transporting layer and, where the material of interest is an inorganic substance, a process such as sputtering, electron beam deposition, and plasma CVD can also be used. The thickness of the hole-injecting layer 3 formed in the aforementioned manner is normally 3 to 100 nm, preferably 5 to 50 nm.

The cathode 7 plays a role of injecting electrons into the light-emitting layer 5. A material useful for the cathode may be the same as the aforementioned material for the anode 2. However, a metal of low work function is preferable for efficient injection of electrons and a metal such as tin, magnesium, indium, calcium, aluminum, and silver or an alloy thereof may be used. Concrete examples are alloy electrodes of low work function such as magnesium-silver alloys, magnesium-indium alloys, and aluminum-lithium alloys.

The thickness of the cathode 7 is usually the same as that for the anode 2. Protection of the cathode made from a metal of low work function by covering with a layer of a metal of high work function that is stable toward the air improves the stability of the device. A metal such as aluminum, silver, copper, nickel, chromium, gold, and platinum is used for this protection.

Furthermore, insertion of an ultrathin insulating film (0.1 to 5 nm) of LiF, $MgF_2$, $Li_2O$, and the like as an electron-injecting layer between the cathode and the electron-transporting layer is also an effective method for improving the efficiency of the device.

It is possible to fabricate a device having a structure that is the reverse of the structure shown in FIG. 1; that is, a device is fabricated by piling the cathode 7, the electron-transporting layer 6, the light-emitting layer 5, the hole-transporting layer 4, and the cathode 2 in this order one upon another on the substrate 1. As described earlier, it is also possible to dispose the organic EL device of this invention between two substrates at least one of which is highly transparent. In the case of this reverse structure, it is also possible to add or omit layers as needed.

An organic EL device provided by this invention is applicable to a single device, a device with its structure arranged in array, or a device in which the anode and the cathode are arranged in X—Y matrix. This invention provides an organic EL device that is markedly improved in luminous efficiency and driving stability over the conventional devices utilizing emission of light from the singlet state by incorporating a compound of a specified skeleton and a phosphorescent metal complex in the light-emitting layer and the organic El device can perform excellently when applied to full-color or multi-color panels.

Examples

This invention will be described in more detail below with reference to Synthetic Examples and Examples, but will not be limited to the descriptions in these examples unless the descriptions exceed the scope of this invention.

The following abbreviations are used in the examples.
Me8HQ: 2-methyl-8-hydroxyquinoline
Me8HQ-D: deuterated Me8HQ
BAlq: p-phenylphenolato-bis(2-methyl-8-quinolinolato-N1,O8)aluminum
BAlq-D: deuterated BAlq (Compound 1)
AQD: aluminum quinolinol dimer (Compound 20)
AQD-D: deuterated AQD (Compound 21)

(Compound 20)

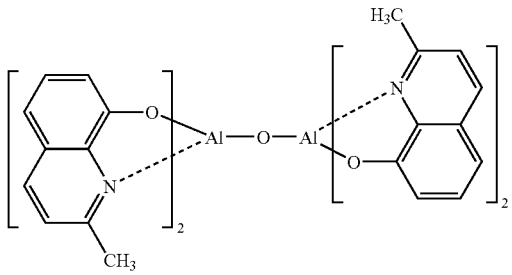

Synthetic Example 1

In a 100-ml autoclave were placed 8.0 g of Me8HQ, 77 g of heavy water, and 0.1 g of a palladium(10%)/carbon catalyst and the mixture was heated at 180° C. with stirring for 2 hours to allow the reaction to proceed. Upon completion of the reaction, the catalyst was filtered off, toluene was added to the remaining mixture to effect oil-water separation, and the aqueous layer was extracted with toluene. The organic layer was dried over anhydrous magnesium sulfate and the solvent was removed to give a crude product. The crude product was purified by distillation under reduced pressure to give 7.6 g of Me8HQ-D. The yield was 92%.

Synthetic Example 2

In a 200-ml autoclave were placed 16.0 g of Me8HQ, 140 g of heavy water, and 0.016 g of a palladium(10%)/carbon catalyst and the mixture was heated at 180° C. with stirring for 2 hours to allow the reaction to proceed. The reaction product was separated and purified as in Synthetic Example 1 to give 14.6 g of Me8HQ-D. The yield was 88%.

Synthetic Example 3

In a 200-ml autoclave were placed 16.0 g of Me8HQ, 140 g of heavy water, and 0.016 g of a palladium(10%)/carbon catalyst and the mixture was heated at 140° C. with stirring for 2 hours to allow the reaction to proceed. The reaction product was separated and purified as in Synthetic Example 1 to give 14.9 g of Me8HQ-D. The yield was 90%.

The compounds Me8HQ-Ds obtained in Synthetic Examples 1, 2, and 3 are hereinafter respectively referred to as Me8HQ-D1, Me8HQ-D2, and Me8HQ-D3. The compound designated as Me8HQ-D refers to any of the compounds represented by formula (IV) wherein $R_1$ to $R_5$ are either H or D. As shown in Table 1, Me8HQ-D1, Me8HQ-D2, and Me8HQ-D3 differ from one another in the degree of deuteration.

The degree of deuteration of hydrogen atoms in each of Me8HQ-D1, Me8HQ-D2, and Me8HQ-D3 was calculated by integrating the NMR spectral data while using hexamethylbenzene as a standard material. The results are shown in Table 1. In the table, 2-CH3 denotes the methyl group at position 2 and 3-H denotes the hydrogen atom at position 3.

TABLE 1

| Synthetic example | Degree of deuteration | | | | | |
|---|---|---|---|---|---|---|
| (Me8HQ-D) | 2-CH$_3$ | 3-H | 4-H | 5-H | 6-H | 7-H |
| 1 (Me8HQ-D1) | 97% | 34% | 29% | 68% | 33% | 92% |
| 2 (Me8HQ-D2) | 96% | 18% | 13% | 62% | 19% | 90% |
| 3 (Me8HQ-D3) | 47% | 9%* | 8% | 9%* | 11% | 24% |

*Mean value of positions 3 and 5

Figure 2:
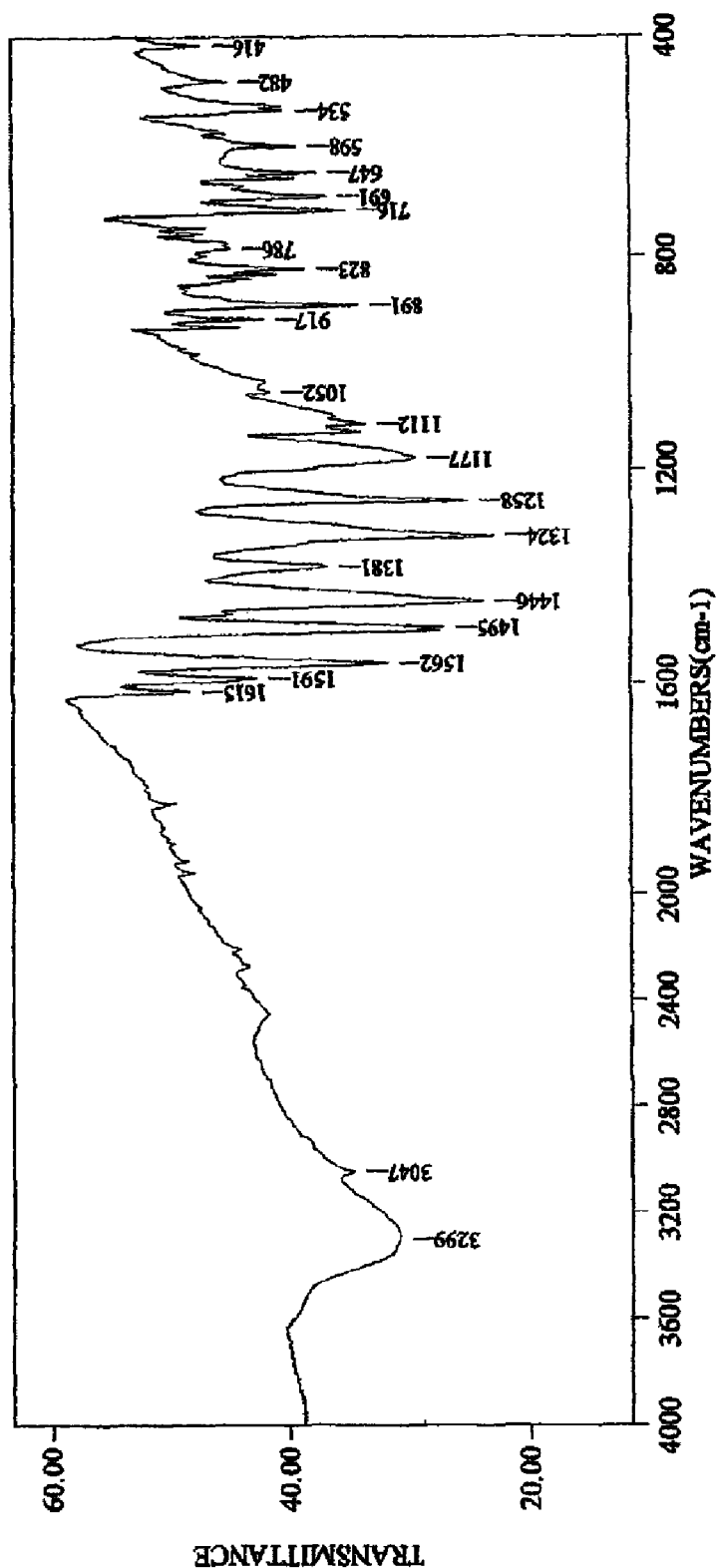
FIG. 2 is the IR spectrum of Me8H-D1.
Figure 3:
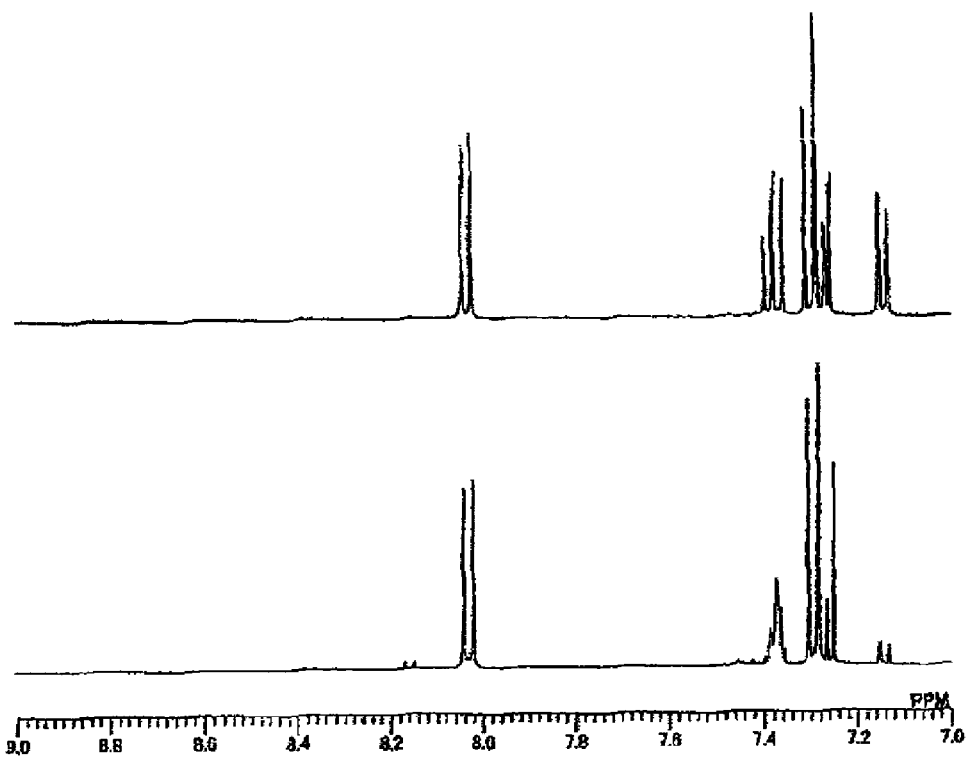
FIG. 3 shows the NMR spectra (δ 7.0-9.0) of Me8HQ and Me8H-D1.
Figure 4:
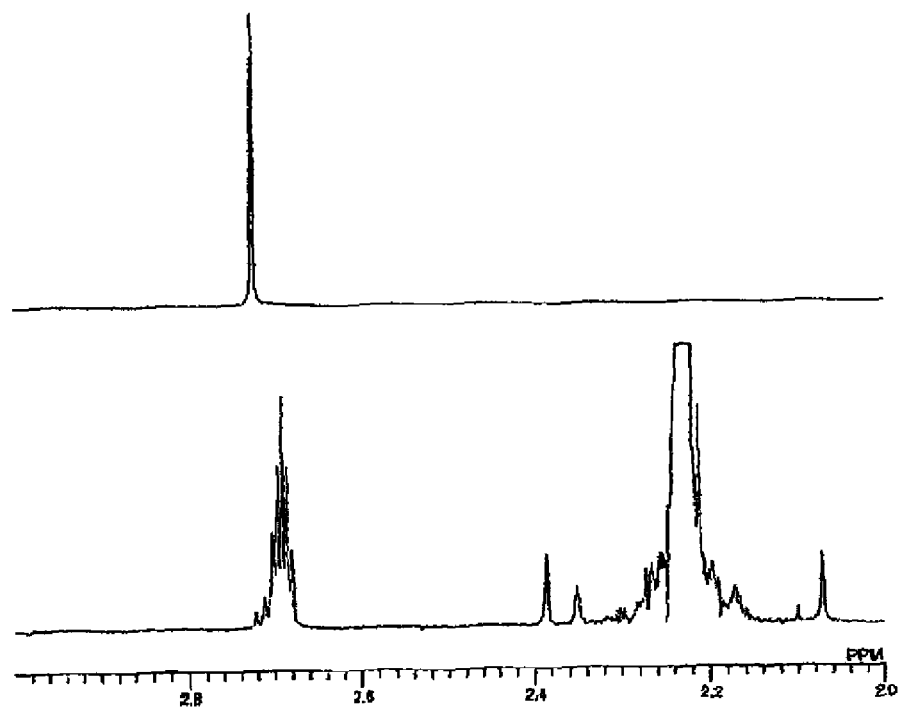
FIG. 4 shows the NMR spectra (δ 2.0-3.0) of Me8HQ and Me8H-D1.

The IR and NMR spectral data are shown in FIGS. 2 to 4 for Me8HQ-D1 obtained in Synthetic Example 1 as an example of Me8HQ-Ds. FIG. 2 shows the IR spectrum. The NMR spectra are shown in FIG. 3 (δ 7.0-9.0) and FIG. 4 (δ 2.0-3.0); in each figure, the upper spectrum refers to the raw material Me8HQ and the lower spectrum to the product Me8HQ-D1. The sample of Me8HQ-D1 contains hexamethylbenzene as a standard material.

Synthetic Example 4

In a 100-ml three-necked flask were placed 1.1 g of Me8HQ-D1 prepared in Synthetic Example 1, 1.2 g of aluminum triisopropoxide, and 20 mL of toluene and the mixture was stirred. To the resulting suspension was added a solution of 2.0 g of 4-hydroxybiphenyl in 12 mL of toluene and the mixture was heated under reflux for 2 hours. After cooling, the precipitate formed was collected by filtration and dried to give 2.7 g of a crude product. The crude product was purified by sublimation to give 2.2 g of BAlq-D. The yield was 71%.

Synthetic Example 5

The reaction was carried out as in Synthetic Example 4 with the exception of using Me8HQ-D2 prepared in Synthetic Example 2 to give 2.1 g of BAlq-D. The yield was 68%.

Synthetic Example 6

The reaction was carried out as in Synthetic Example 4 with the exception of using Me8HQ-D3 prepared in Synthetic Example 3 to give 2.1 g of BAlq-D. The yield was 68%.

The compounds BAlq-Ds obtained in Synthetic Examples 4, 5, and 6 are hereinafter respectively referred to as BAlQ-D4, BAlQ-D5, and BAlQ-D6; they differ from one another in the degree of deuteration because of the difference in the raw material Me8HQ-D.

Figure 5:
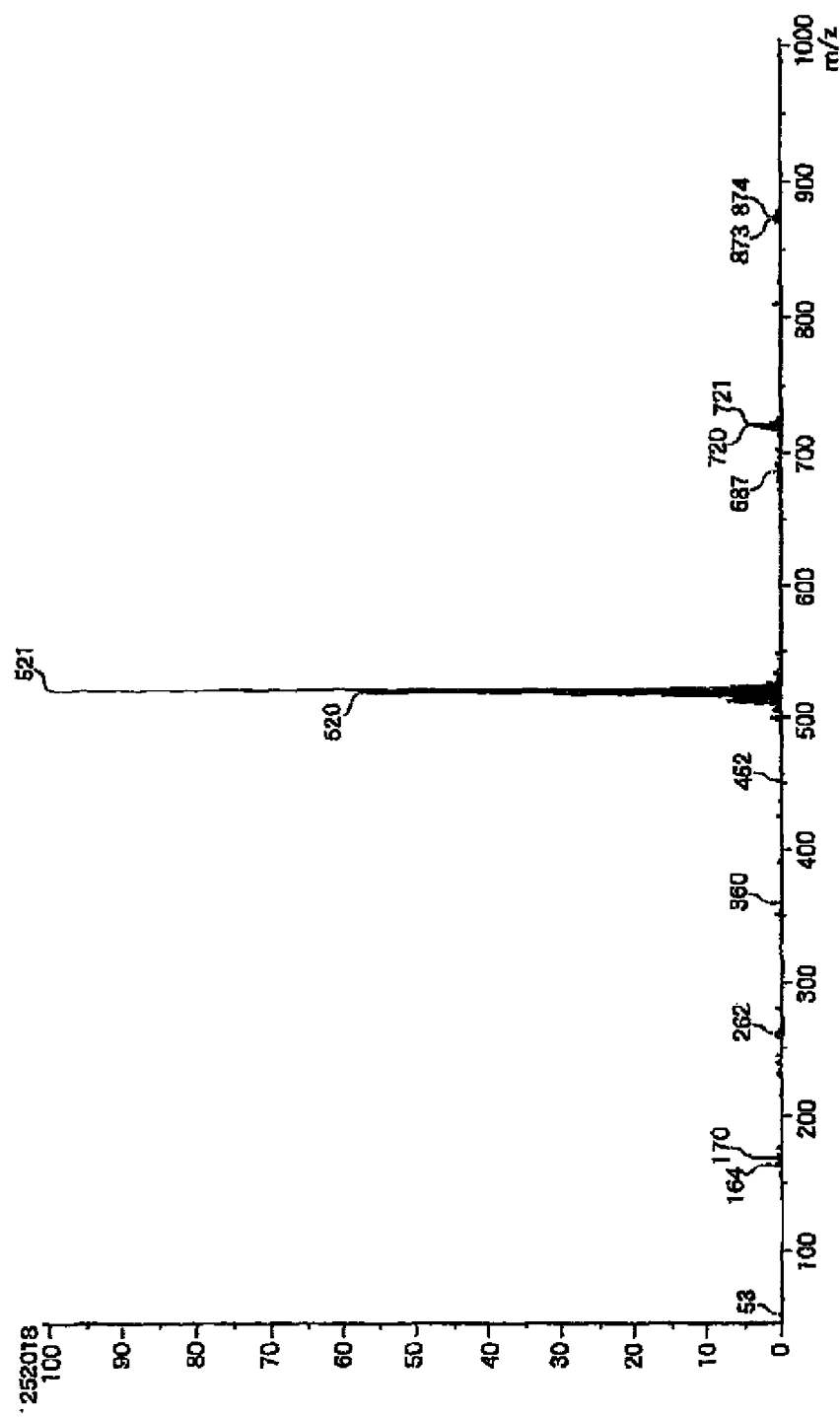
FIG. 5 is the FD-MS spectrum of BAlq-D4.
Figure 6:
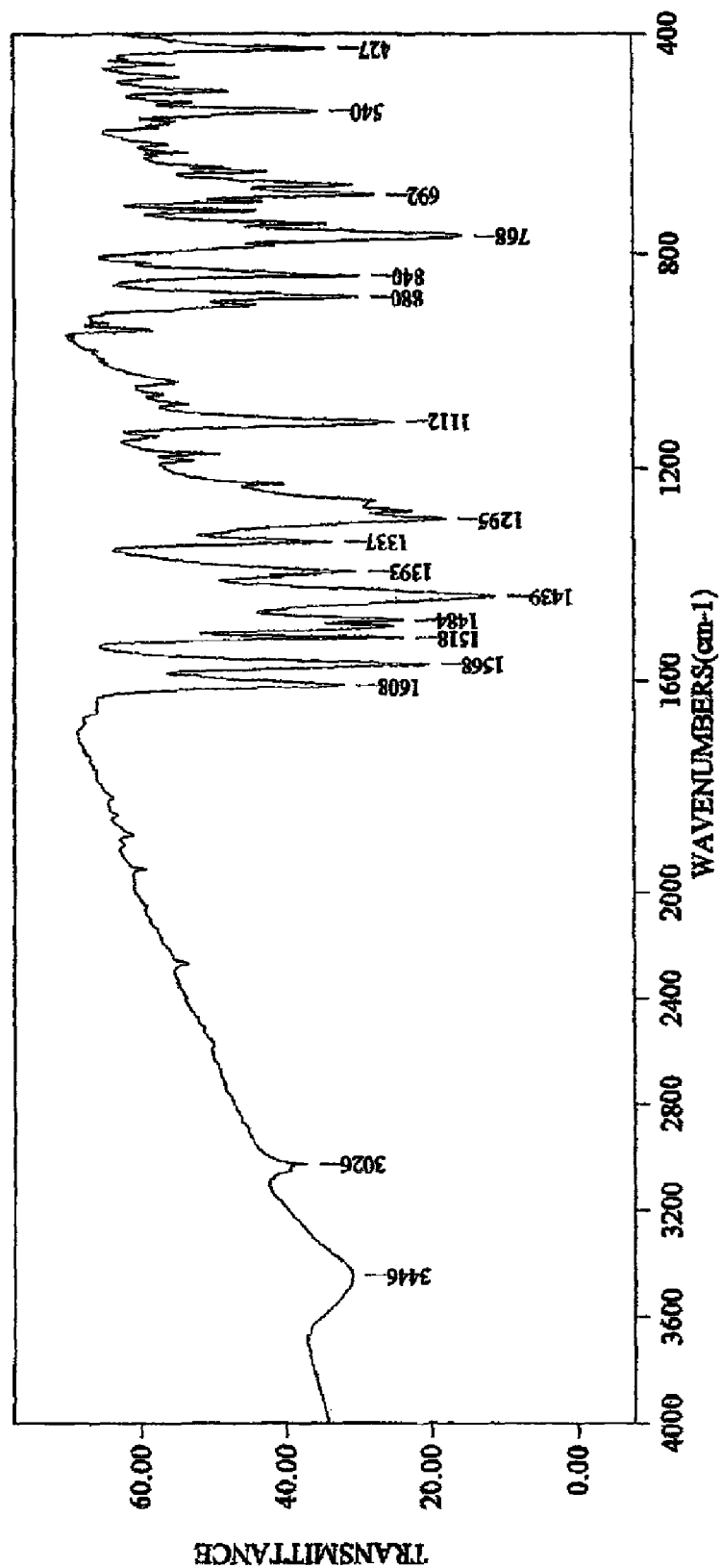
FIG. 6 is the IR spectrum of BAlq-D4.

The FD-MS spectrum and IR spectrum are shown respectively in FIGS. 5 and 6 for BAlq-D4 as an example of BAlq-Ds.

Synthetic Example 7

In a 50-mL three-necked flask were placed 2.0 g of Me8HQ-D1 prepared in Synthetic Example 1, 1.2 g of aluminum triisopropoxide, and 28 mL of dehydrated ethanol and the mixture was heated under reflux for 1 hour. The reaction was stopped by adding 0.1 mL of water to the reaction mixture, the resulting mixture was cooled, and the precipitate formed was collected by filtration and dried to give a crude product. The crude product was purified by sublimation to give 1.6 g of AQD-D. The yield was 37%. When the product was analyzed by mass spectrometry (FD-MS), the parent peaks of 722 (M+19) and 723 (M+20) were observed, but the parent peak of 702 for the undeuterated compound (AQD) was not observed.

Synthetic Example 8

The reaction was carried out as in Synthetic Example 7 with the exception of using Me8HQ-D2 prepared in Synthetic Example 2 to give 1.7 g of AQD-D. The yield was 39%.

Synthetic Example 9

The reaction was carried out as in Synthetic Example 7 with the exception of using Me8HQ-D3 prepared in Synthetic Example 3 to give 1.6 g of AQD-D. The yield was 37%.

The compound designated as AQD-D is identical in chemical formula with Compound 21 and the AQD-Ds obtained in Synthetic Examples 7, 8, and 9 are hereinafter respectively referred to as AQD-D7, AQD-D8, and AQD-D9. They differ from one another in the degree of deuteration because of the difference of the raw material Me8HQ-D.

Figure 7:
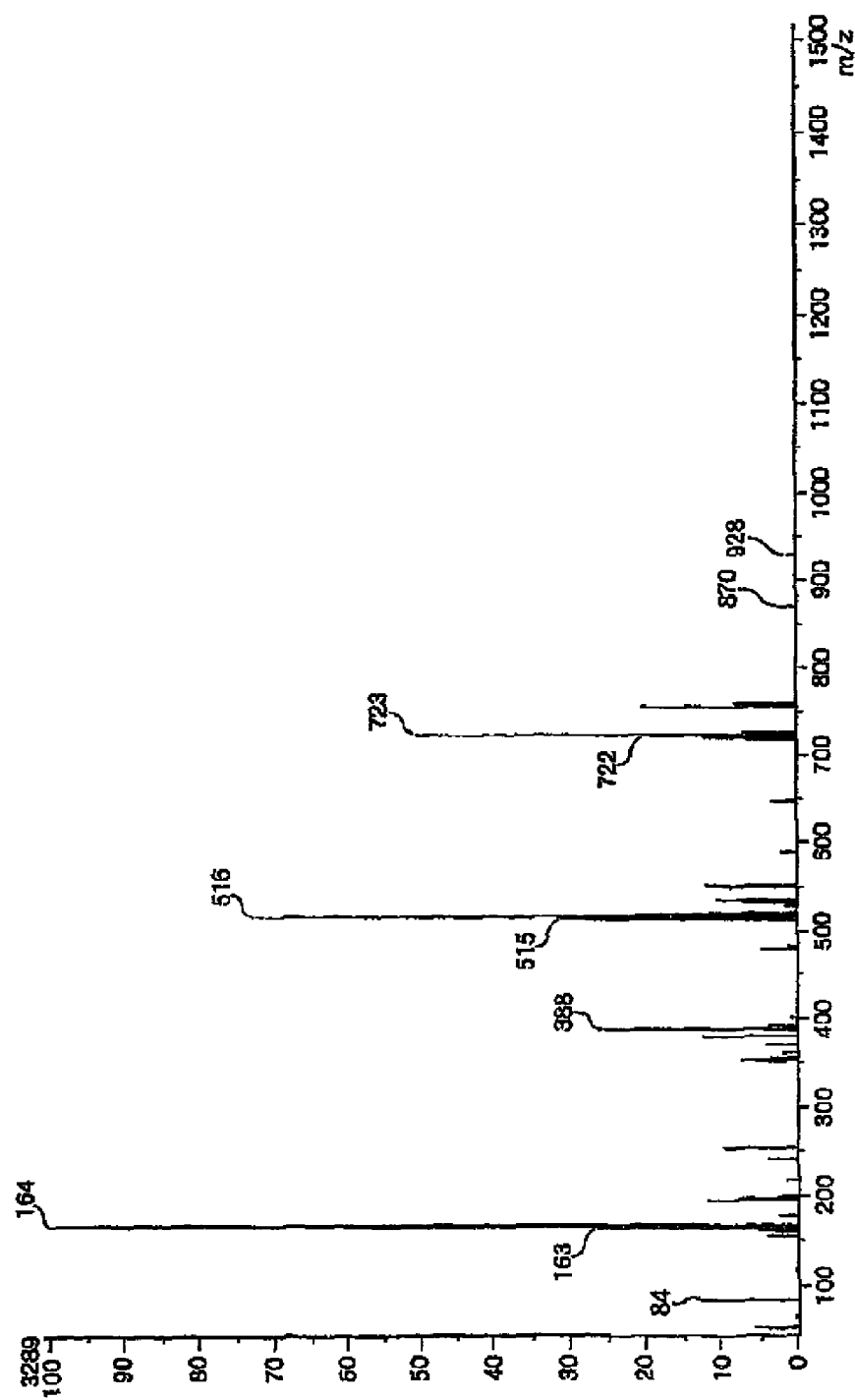
FIG. 7 is the FD-MS spectrum of AQD-D7.
Figure 8:
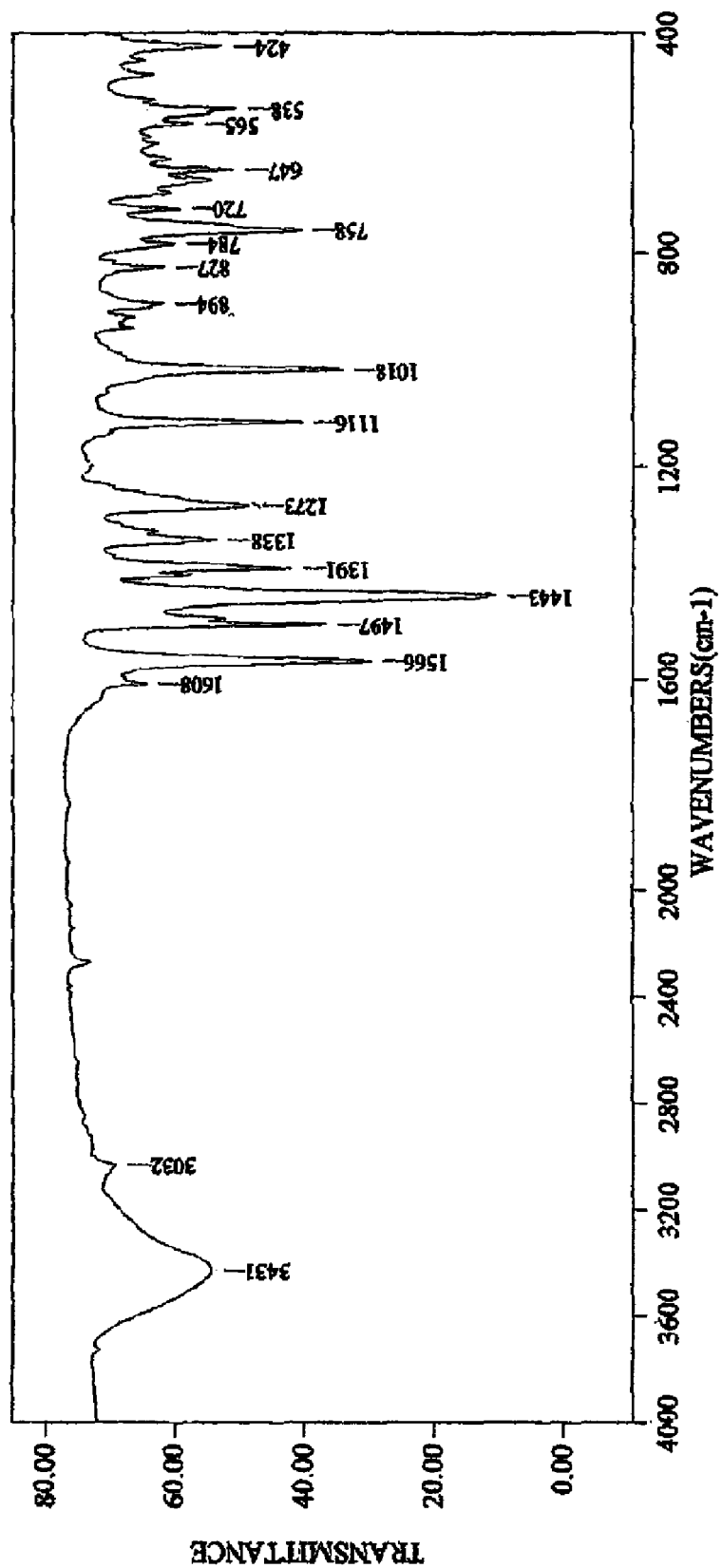
FIG. 8 is the IR spectrum of AQD-D7.

The analytical results of mass spectrometry and IR spectrometry performed on AQD-D7 are shown in FIGS. 7 and 8 as an example of AQD-Ds. FIG. 7 is the FD-MS spectrum of AQD-D7 and FIG. 8 is the IR spectrum of AQD-D7.

Example 1

Copper phthalocyanine (CuPC) was used for the hole-injecting layer, α-NPD for the hole-transporting layer, and Alq3 for the electron-transporting layer. These compounds in thin film were piled one upon another on a glass substrate having formed thereon a 110 nm-thick ITO anode in the following manner by vacuum deposition at a degree of vacuum of $5.0 \times 10^{-4}$ Pa. First, CuPC was deposited on the ITO anode at a rate of 3.0 Å/sec to a thickness of 25 nm to form the hole-injecting layer. Then, α-NPD was deposited on the hole-injecting layer at a rate of 3.0 Å/sec to a thickness of 55 nm to form the hole-transporting layer.

Thereafter, the light-emitting layer was formed on the hole-transporting layer by co-depositing BAlq-D4 obtained in Synthetic Example 4 as a host material and Ir(piq)3 (Compound 44) from different evaporation sources to a thickness of 47.5 nm. The concentration of the Ir(piq)3 at this point was 8.0%.

Following this, Alq3 was deposited at a rate of 3.0 Å/sec to a thickness of 30 nm to form the electron-transporting layer. Further, lithium fluoride (LiF) was deposited on the electron-transporting layer at a rate of 0.1 Å/sec to a thickness of 1 mm to form the electron-injecting layer. Finally, aluminum (Al) was deposited on the electron-injecting layer at a rate of 10 Å/sec to a thickness of 200 nm to form the electrode thereby completing the fabrication of an organic EL device.

Example 2

An organic EL device was fabricated as in Example 1 with the exception of using BAlq-D5 obtained in Synthetic Example 5 as a host material in the light-emitting layer.

Example 3

An organic EL device was fabricated as in Example 1 with the exception of using BAlq-D6 obtained in Synthetic Example 6 as a host material in the light-emitting layer.

Comparative Example 1

An organic EL device was fabricated as in Example 1 with the exception of using undeuterated BAlq as a host material in the light-emitting layer.

The luminous peak wavelength, the maximum luminous efficiency, and the luminance half-life (initial luminance, 2,000 cd/m$^2$) are shown in Table 2 for the organic EL devices fabricated in Examples 1 to 3 and Comparative Example 1.

TABLE 2

|  | Luminous peak wavelength (nm) | Maximum luminous efficiency (cd/A) | Luminance half-life (hr) |
| --- | --- | --- | --- |
| Example 1 | 620 | 9.2 | 2000 |
| Example 2 | 620 | 9.2 | 2000 |
| Example 3 | 620 | 9.0 | 1800 |
| Comparative example 1 | 620 | 8.8 | 1500 |

Example 4

Copper phthalocyanine (CuPC) was used for the hole-injecting layer, α-NPD for the hole-transporting layer, and Alq3 for the electron-transporting layer. These compounds in thin film were piled one upon another on a glass substrate having formed thereon a 110 nm-thick ITO anode in the following manner by vacuum deposition at a degree of vacuum of $5.0 \times 10^{-4}$ Pa. First, CuPC was deposited on the ITO anode at a rate of 3.0 Å/sec to a thickness of 25 nm to form the hole-injecting layer. Then, α-NPD was deposited on the hole-injecting layer at a rate of 3.0 Å/sec to a thickness of 55 nm to form the hole-transporting layer.

Thereafter, the light-emitting layer was formed on the hole-transporting layer by co-depositing AQD-D7 obtained in Synthetic Example 7 as a host material and Ir(piq)3 (Compound 44) from different evaporation sources to a thickness of 47.5 nm. The concentration of the Ir(piq)3 at this point was 8.0%.

Following this, Alq3 was deposited at a rate of 3.0 Å/sec to a thickness of 30 nm to form the electron-transporting layer. Further, lithium fluoride (LiF) was deposited on the electron-transporting layer at a rate of 0.1 Å/sec to a thickness of 1 mm to form the electron-injecting layer. Finally, aluminum (Al) was deposited on the electron-injecting layer at a rate of 10 Å/see to a thickness of 200 nm to form the electrode thereby completing the fabrication of an organic EL device.

Example 5

An organic EL device was fabricated as in Example 4 with the exception of using AQD-D8 that was obtained in Synthetic Example 8 and different in the degree of deuteration from AQD-D7 as a host material in the light-emitting layer.

Example 6

An organic EL device was fabricated as in Example 4 with the exception of using AQD-D9 that was obtained in Synthetic Example 9 and different in the degree of deuteration from AQD-D7 as a host material in the light-emitting layer Comparative Example 2

An organic EL device was fabricated as in Example 1 with the exception of using undeuterated AQD as a host material in the light-emitting layer.

The luminous peak wavelength, the maximum luminous efficiency, and the luminance half-life (initial luminance, 2,000 cd/m²) are shown in Table 3 for the organic EL devices fabricated in Examples 4 to 6 and Comparative Example 2.

TABLE 3

| | Luminous peak wavelength (nm) | Maximum luminous efficiency (cd/A) | Luminance half-life (hr) |
|---|---|---|---|
| Example 4 | 620 | 9.0 | 1500 |
| Example 5 | 620 | 9.0 | 1500 |
| Example 6 | 620 | 8.8 | 1200 |
| Comparative example 2 | 620 | 8.5 | 1000 |

INDUSTRIAL APPLICABILITY

This invention provides an organic EL device that shows a long driving life while maintaining good luminous characteristics. Accordingly, the organic EL device provided by this invention is potentially applicable to flat panel displays (for example, office computers and wall-hanging television sets), vehicle display devices, mobile phone displays, light sources utilizing the characteristics of planar light emitters (for example, light sources of copiers and backlight sources of liquid crystal displays and instruments), signboards, and beacon lights and has a high technical value.

The invention claimed is:

1. An organic electroluminescent device material comprising an organic metal complex represented by the following general formula (I)

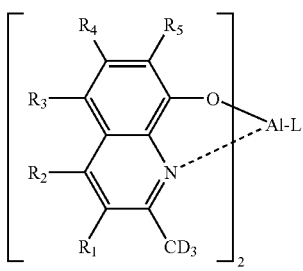

wherein, $R_1$ to $R_5$ each is independently a monovalent substituent selected from hydrogen atoms, deuterium atoms, alkyl groups, aralkyl groups, alkenyl groups, a cyano group, alkoxy groups, substituted or unsubstituted aromatic hydrocarbon groups and substituted or unsubstituted aromatic heterocyclic groups; in the case where the monovalent substituent has hydrogen atoms, the hydrogen atoms may be deuterium atoms and D is a deuterium atom; L is a monovalent group represented by the following formula (1), (2), (3), or (4)

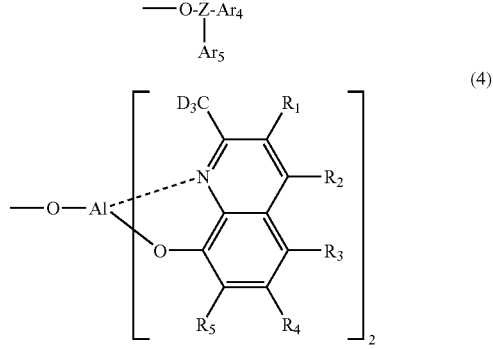

in which $Ar_1$ to $Ar_5$ each is independently a substituted or unsubstituted aromatic hydrocarbon group or a substituted or unsubstituted aromatic heterocyclic group, Z is silicon or germanium, and $R_1$ to $R_5$ and D are as defined in general formula (I).

2. An organic electroluminescent device material as described in claim 1 wherein the organic metal complex is represented by the following general formula (II)

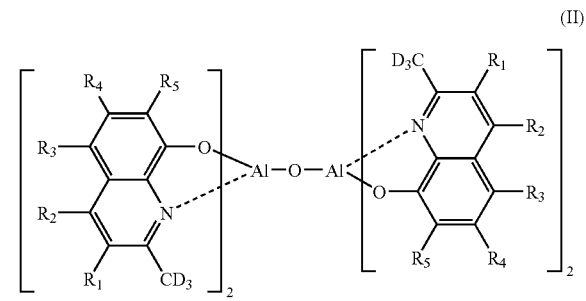

in which $R_1$ to $R_5$ and D are as defined in general formula (I).

3. An organic electroluminescent device comprising an anode, an organic layer containing a hole-transporting layer, a light-emitting layer, and an electron-transporting layer, and a cathode piled one upon another on a substrate wherein at least one of the layers in the organic layer comprises the organic electroluminescent device material described in claim 1.

4. An organic electroluminescent device comprising an anode, an organic layer containing a hole-transporting layer, a light-emitting layer, and an electron-transporting layer, and a cathode piled one upon another on a substrate wherein the hole-transporting layer is disposed between the light-emitting layer and the anode, the electron-transporting layer is disposed between the light-emitting layer and the cathode, and the light-emitting layer comprises the organic electroluminescent device material described in claim 1.

5. An organic electroluminescent device as described in claim 4 wherein the light-emitting layer comprises the organic electroluminescent device material as a host material and an organic metal complex containing at least one metal selected from groups 7 to 11 of the periodic table as a guest material.

6. An organic electroluminescent device as described in claim 5 wherein a hole-injecting layer is disposed between the anode and the hole-transporting layer and an electron-injecting layer is disposed between the cathode and the electron-transporting layer.

\* \* \* \* \*